(12) United States Patent
Jung et al.

(10) Patent No.: US 11,375,933 B2
(45) Date of Patent: Jul. 5, 2022

(54) BIO-SENSOR AND MANUFACTURING METHOD THEREFOR

(71) Applicant: SAMSUNG ELECTRONICS CO., LTD., Suwon-si (KR)

(72) Inventors: Hyun-joo Jung, Yongin-si (KR); Kwang-bok Kim, Incheon (KR); Seong-je Cho, Suwon-si (KR); Kyoung-jin Moon, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 426 days.

(21) Appl. No.: 16/611,565

(22) PCT Filed: May 15, 2018

(86) PCT No.: PCT/KR2018/005540
§ 371 (c)(1),
(2) Date: Nov. 7, 2019

(87) PCT Pub. No.: WO2018/212550
PCT Pub. Date: Nov. 22, 2018

(65) Prior Publication Data
US 2021/0077001 A1    Mar. 18, 2021

Related U.S. Application Data

(60) Provisional application No. 62/507,406, filed on May 17, 2017.

(30) Foreign Application Priority Data

Nov. 6, 2017  (KR) .................. 10-2017-0146928

(51) Int. Cl.
| | |
|---|---|
| A61B 5/1486 | (2006.01) |
| A61B 5/00 | (2006.01) |
| C12Q 1/00 | (2006.01) |
| A61B 5/145 | (2006.01) |
| C25D 9/02 | (2006.01) |
| C12N 9/12 | (2006.01) |
| C12N 9/10 | (2006.01) |
| C12N 11/14 | (2006.01) |
| C12N 9/04 | (2006.01) |

(52) U.S. Cl.
CPC ...... *A61B 5/14865* (2013.01); *A61B 5/14532* (2013.01); *A61B 5/6848* (2013.01); *C12N 9/0006* (2013.01); *C12N 9/1096* (2013.01); *C12N 9/1205* (2013.01); *C12N 11/14* (2013.01); *C12Q 1/001* (2013.01); *C12Q 1/005* (2013.01); *C12Q 1/006* (2013.01); *C25D 9/02* (2013.01); *A61B 2562/125* (2013.01)

(58) Field of Classification Search
CPC ....... C12N 11/06; C12N 11/08; C12N 11/089; C12N 11/14; C12Q 1/001; C12Q 1/004; C12Q 1/005; C12Q 1/006
See application file for complete search history.

(56) References Cited

U.S. PATENT DOCUMENTS

2013/0224795 A1   8/2013  Park et al.
2016/0100778 A1   4/2016  Yi et al.

FOREIGN PATENT DOCUMENTS

| KR | 10-1987-0009230 A | 10/1987 |
|---|---|---|
| KR | 10-2000-0000791 A | 1/2000 |
| KR | 10-1257996 B1 | 4/2013 |
| KR | 10-2016-0135104 A | 11/2016 |
| WO | 2005/092920 A1 | 10/2005 |

OTHER PUBLICATIONS

Machine English translation of KR 101257996 B1, published Apr. 30, 2013, 13 pags, (Year: 2013).*
High resolution images of Figs 1-5 and 9 from KR 101257996 B1, downloaded from the WIPO. (Year: 2013).*
Kan et al., "Boronate Complex Formation with Dopa Containing Mussel Adhesive Protein Retards pH-Induced Oxidation and Enables Adhesion to Mica", PLOS One, vol. 9, Issue 10, e108869, Oct. 10, 2014, pp. 1-7, 8 pages total.
Li et al., "Mussel-inspired Hydrogels for Biomedical and Environmental Applications", Polymer Chemistry, Nov. 3, 2014, pp. 1-6, 7 pages total.
Magdziak et al., "Regioselective Oxidation of Phenols to o-Quinones with o-Iodoxybenzoic Acid (IBX)", Org Lett., 4 (2), Jan. 24, 2002, 9 pages total.
Li et al., "Electrochemical quartz crystal microbalance study on growth and property of the polymer deposit at gold electrodes during oxidation of dopamine in aqueous solutions", Thin Solid Films, 497 (2006), Dec. 1, 2005, pp. 270-278, 9 pages total.
Cencer et al., "Effect of pH on the Rate of Curing and Bioadhesive Properties of Dopamine Functionalized Poly(ethylene glycol) Hydrogels", Biomacromolecules, 15, Jul. 10, 2014, pp. 2861-2869, 9 pages total.
Guan et al., "Effective immobilization of tyrosinase via enzyme catalytic polymerization of L-DOPA for highly sensitive phenol and atrazine sensing", Talanta, 160, Jul. 4, 2016, pp. 125-132, 8 pages total.
International Search Report dated Aug. 30, 2018 issued by the International Searching Authority in counterpart International Application No. PCT/KR2018/005540 (PCT/ISA/210).
Written Opinion dated Aug. 30, 2018 issued by the International Searching Authority in counterpart International Application No. PCT/KR2018/005540 (PCT/ISA/237).

* cited by examiner

*Primary Examiner* — Thane Underdahl
(74) *Attorney, Agent, or Firm* — Sughrue Mion, PLLC

(57) ABSTRACT

Disclosed is a manufacturing method for a bio-sensor. The present manufacturing method comprise the steps of: preparing an acidic solution comprising an enzyme and a molecule containing a catechol group; an immersing electrodes in the acidic solution and applying a voltage to the electrodes, thereby attaching a structure, which is generated by a reaction of the enzyme and the molecule containing a catechol group, to the electrodes.

13 Claims, 12 Drawing Sheets

| Glucose (mg·dL⁻¹) | Day 1 | Day 2 | Day 3 | Day 4 | Day 5 | Day 6 | Day 7 | Current Avg.(nA) | Cv (%) |
|---|---|---|---|---|---|---|---|---|---|
| 0 | 4.36 | 4.01 | 3.64 | 3.48 | 3.44 | 3.22 | 3.31 | 3.64 | - |
| 100 | 6.4 | 6.17 | 5.87 | 5.37 | 5.67 | 5.71 | 5.69 | 5.84 | 5.84 |
| 200 | 8.99 | 8.48 | 8.17 | 7.98 | 7.71 | 7.84 | 7.88 | 8.15 | 4.97 |
| 300 | 12.16 | 11.71 | 11.34 | 11.19 | 11.21 | 11.14 | 11.11 | 11.41 | 3.79 |
| 400 | 16.46 | 15.51 | 15.07 | 14.87 | 14.97 | 14.55 | 14.64 | 15.15 | 4.67 |
| | | | | | | | | | 4.82 |

BIO-SENSOR AND MANUFACTURING METHOD THEREFOR

CROSS REFERENCE TO RELATED APPLICATIONS

This application is a National Stage of International Application No. PCT/KR2018/005540, filed May 15, 2018, claiming priority based on U.S. Provisional Patent Application No. 62/507,406, filed May 17, 2017, and Korean Patent Application No. 10-2017-0146928, filed Nov. 6, 2017, the contents of all of which are incorporated herein by reference in their entirety.

TECHNICAL FIELD

The present disclosure relates to a bio-sensor and a manufacturing method of a bio-sensor, and more specifically, to a bio-sensor and a manufacturing method of a bio-sensor capable of ensuring reproducibility even in continuous measurements.

BACKGROUND ART

Determining an analyte dose in biological fluids is useful in a diagnosis and a treatment of physiological abnormalities. For example, a glucose (for example, blood glucose) level must be checked regularly in the diagnosis and prevention of diabetes.

Conventionally, an electrochemical method using biosensors have been mainly used. An electrochemical bio-sensor is an apparatus that measures an amount of target material for measurement by a method of detecting electrochemical signals through enzyme reaction with the target material for measurement by using an enzyme electrode, in which enzymes are immobilized on the electrodes.

The bio-sensor may be capable of measuring the amount of target material for measurement through various methods, among which is a method that requires drawing blood, which includes the problems of the measured value of blood glucose changing according to the proficiency of drawing blood method, and the impossibility of perfectly detecting a change in concentration of the subject material for measurement in the blood by a few intermittent measurements.

Accordingly, an apparatus capable of monitoring the concentration of the subject material for measurement accurately without drawing blood has been developed recently, and a fully implantable type that implants the bio-sensor itself fully in a body and a minimally invasive method of inserting a needle-shaped sensor capable of being inserted to a subcutaneous tissue are the generally used methods.

The bio-sensor of the minimally invasive method, by being inserted into the subcutaneous tissue rather than a blood vessel, may avoid direct contact with blood and thus may operate for a number of days being manufactured as a bio-compatible material, and is advantageous for being able to be inserted by a patient without surgery by a professional.

However, based on measuring glucose in bio-fluids with the bio-sensor of such a minimally invasive method, because the bio-sensor exists continuously in the skin in an inserted state, problems such as enzymes separating from electrodes into the bio-fluids according to long term use may occur and inaccurate values may be measured.

Accordingly, based on the enzyme being immobilized on the electrode, development of a bio-senor capable of showing superior reproducibility even in continuous measurements is required.

DISCLOSURE

Technical Problem

The present disclosure has been conceived to resolve the above-described problems, and the object thereof is to provide a bio-senor and a manufacturing method of the bio-sensor capable of ensuring reproducibility even in continuous measurements.

Technical Solution

A manufacturing method of a bio-sensor according to an embodiment of the present disclosure to achieve the above-mentioned object, includes preparing an acidic solution including a molecule containing a catechol group and an enzyme and attaching a structure produced by the molecule containing the catechol group reacting with the enzyme by immersing an electrode in the acidic solution and applying a voltage to the electrode.

In this case, a pH of the acidic solution is pH4 to pH 6.

The structure is produced by binding the molecule including a Quinone methide group derived by electrochemically oxidizing the molecule containing the catechol group in an acidic environment with the enzyme.

The attaching includes applying a voltage to the electrode by Cyclic voltammetry.

The attaching includes applying a pulse type voltage to the electrode.

The attaching includes applying a predetermined constant voltage to the electrode.

The molecule containing the catechol group is derived from a mussel adhesive protein.

The manufacturing method of a bio-sensor according an embodiment, further includes manufacturing a needle shaped electrode to be invasive to skin.

The enzyme is selected from a group consisting of glucose oxidase, glucose dehydrogenase, Hexokinase, Glutamic-oxaloacetic transaminase and Glutamic-pyruvic transaminase.

A bio-sensor according to one embodiment of the present disclosure includes an electrode and a structure attached to a surface of the electrode and formed by binding a molecule comprising Quinone methide group with an enzyme.

In this case, the molecule including the Quinone methide group is derived by electrochemically oxidizing the molecule containing the catechol group in an acidic environment.

The electrode is needle shaped to be invasive to skin.

The enzyme is selected from a group consisting of glucose oxidase, glucose dehydrogenase, Hexokinase, Glutamic-oxaloacetic transaminase and Glutamic-pyruvic transaminase.

DESCRIPTION OF DRAWINGS

FIG. 7(*b*) is a SEM image provided to show an electrochemically oxidized Mgfp-3 and glucose oxidase reacting and forming a smooth interface on the surface of an electrode under optimized acidic conditions;

DETAILED DESCRIPTION OF EXEMPLARY EMBODIMENTS

Hereinafter, the present disclosure will be more specifically described with reference to the accompanying drawings. In describing the disclosure, a detailed description of the related art concerning a known function or configuration is omitted when it is determined that the detailed description may unnecessarily obscure the gist of the disclosure. In addition, the terms described below are terms that have been defined considering its function in the present disclosure and may change depending the intention or relationship of the user or the operator. Accordingly, it is to be understood that the definition thereof is to be defined based on the content throughout the overall specification. Further, the accompanying drawings are not shown in actual scale but measurements of some elements may be shown exaggerated to assist in the understanding of the present disclosure.

The bio-sensor is an apparatus capable of measuring a target material through an electrochemical method by using a biological material such as enzymes having specific detecting ability on materials for analysis. Although the term bio-sensor is used, the apparatus may be variously called such as a sensor, a measuring apparatus, a measuring apparatus, or the like. Further, based on the subject of measurement, the apparatus may be called by various names such as a hydrogen peroxide sensor, a glucose sensor, a blood glucose sensor, or the like.

Movement of electrons by the biochemical oxidization and reduction reaction occurring at the surface of the electrode of the bio-sensor is generated, and by monitoring the current generated by movement of such electrons, the concentration of the target material in the sample may be measured.

The bio-sensor may include a working electrode and a counter electrode (or a counter/reference electrode). In addition, the bio-sensor may include a working electrode, a counter electrode, and a separated reference electrode.

The working electrode is an electrode immobilized with an enzyme, and may be designated as an immobilized enzyme electrode or an enzyme electrode. The enzyme may be selected from a group consisting of glucose oxidase (GOx), glucose dehydrogenase (GDH), Hexokinase, Glutamic-oxaloacetic transaminase, and Glutamic-pyruvic transaminase, but are not limited thereto.

For example, based on the material for detection being glucose, if glucose oxidase enzyme and glucose are reacted, the material would be oxidized to gluconic acid. Further, oxygen or the oxidized medium during the oxidation of glucose would be changed to hydrogen peroxide or the reduced medium, and glucose may be quantified by measuring the current generated by the movement of electrons when the above is oxidized again and returned to the original oxidized form.

Figure 1:
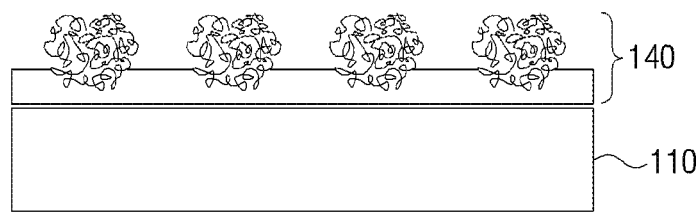
FIG. 1 is a diagram provided to show an electrode of a bio-sensor according to an embodiment of the present disclosure.

FIG. 1 shows a cross-sectional view provided to explain an example of a working electrode with an immobilized enzyme from the electrodes of a bio-sensor.

Referring to FIG. 1, the bio-sensor may include an electrode 110 disposed with a structure 140, which includes an enzyme, on the surface thereof.

The electrode 110 may be manufactured to be needle shaped to be invasive into the skin. Based on inserting the electrode 110 into the skin, it may be possible to continuously measure blood glucose. However, the present disclosure is not limited to this shape, and may have various shapes appropriate to the measurement environment.

The electrode 110 may is consisted of metals such as carbon, gold, platinum, silver, copper, palladium or metal alloys.

The structure 140 including enzyme may be disposed on the electrode 110. The structure 140 may be formed by binding a molecule including a Quinone methide group with an enzyme.

Specifically, the structure 140 including an enzyme may be formed by deriving the molecule including the quinone methide group by electrochemically oxidizing a molecule containing a catechol group in an acidic environment, and by covalently bonding the molecule including the Quinone methide group with the enzyme. The molecule containing the catechol group may be derived from, for example, a mussel adhesive protein.

Mussels are capable of firmly attaching itself to rocks under the sea or the like by producing and secreting adhesive proteins. Specifically, adhesive strength may be maintained even in a wet state. Mussel adhesive protein is capable of attaching to various surfaces such as plastic, glass, metal, Teflon and biomaterials.

Mussel adhesive proteins may be applicable to skin invasive bio-sensors for not attacking human cells or cause an immune reaction, and may be firmly attached to the electrode 110 by forming a covalent bond with an enzyme. That is, the mussel adhesive protein may be employed as a medium to immobilize the enzyme on the electrode 110.

The mechanism of the mussel adhesive protein attaching to a surface of a substrate is due to a chemical modification of a tyrosine residue. The tyrosine in the mussel adhesive protein is changed to Dopa by adding OH groups through a hydration process, and the catechol group, which is a functional group of the Dopa, performs a main role in the attachment to the surface.

The mussel adhesive protein capable of being used in the present disclosure includes a mussel adhesive protein derived from Mytilus edul is, Mytilus galloprovincialis or Mytilus coruscus or variants thereof, but are not limited thereto. For example, the mussel adhesive protein capable of being used in the present disclosure may include fp (foot protein)-1 to fp-5 proteins or variants thereof each derived from the mussel species above.

In the present disclosure, not only molecules derived from mussel adhesive proteins but any molecules containing the catechol group may be used. For example, a molecule including Dopamine, epinephrine, norepinephrine, 1,2-dihydroxybezoic acid, 3,4-dihydroxybenzoic acid and the like may be used as functional groups.

The catechol group becomes a Quinine group if electrochemically oxidized, and the Quinine group may be converted to a Quinone methide group in an acidic environment. The structure 140 produced by covalently bonding at least one from an amine group and a thiol group of an enzyme and a molecule including the Quinone methide group may be firmly attached to the electrode 110. The enzyme in the structure 140 may be strongly bonded through a covalent bond, and since the enzyme may also be attached to the electrode 110 in a state cross-linked with each other between the molecules, the enzyme may be prevented from separating to the outside despite long-term use of the bio-sensor.

Figure 2:
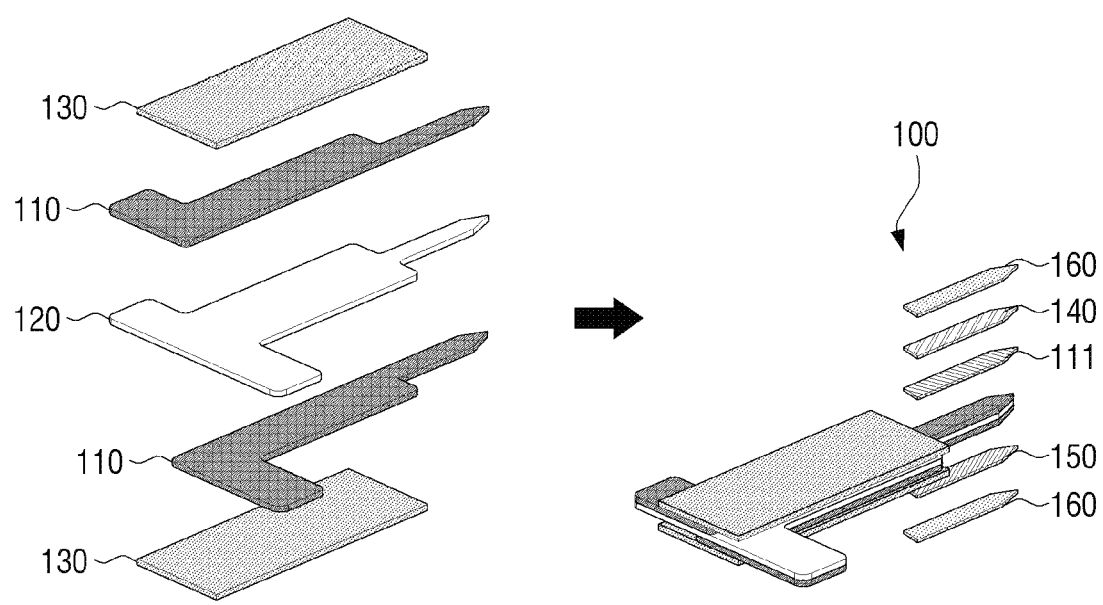
FIG. 2 is a diagram provided to show a configuration of a bio-sensor according to an embodiment of the present disclosure.

FIG. 2 is a diagram provided to describe a configuration of a bio-sensor according to an embodiment of the present disclosure. The content described if FIG. 1 may be applied to FIG. 2 even if the content is omitted in describing FIG. 2.

The bio-sensor 100 may include a structure 140 including a main substrate 120, a working electrode 110, an insulation layer 130, an electron-transfer mediator 111, and an enzyme, a reference electrode 150, and a protective layer 160.

Referring to FIG. 2, the main substrate 120 may be manufactured by cutting the polymer film to a needle shape. The working electrode 110 is disposed on the bottom surface and the top surface of the main substrate 120. Materials consisting the working electrode 110 may be selected from metals such as carbon, gold, platinum, silver, copper, palladium, or the like or metal alloys, but are not limited thereto. Further, an insulation layer 130 may be disposed on the working electrode 110.

The structure 140 including the electron-transfer mediator 111 and the enzyme is immobilized on the working electrode 110. The electron-transfer mediator 111 is to increase electron transfer efficiency from the enzyme to the working electrode 110, and ferrocene, ferrocene derivative, quinine, quinine derivative, transition metal-containing organic material and inorganic material (for example, hexamine ruthenium, osmium-containing polymer, potassium ferricyanide, and the like) or organic conducting salt, viologen may be used. Meanwhile, the electron-transfer mediator 111 in FIG. 2 may be disposed below the structure 140, and the electron-transfer mediator 111 and the structure 140 may exist in a mixed state with each other without a differentiated interface.

The reference electrode 150 may be disposed on an insulation layer 130. The reference electrode 150 allows a constant potential to be applied to the working electrode 110, and current is blocked toward the electrode by the high impedance. The reference electrode 150 may use, for example, a standard hydrogen electrode (SHE), a Calomel, Hg/Hg2Cl2 electrode, silver-silver chloride (Ag/AgCl) electrode. As these have a relatively constant potential difference, and a constant electrode potential may be applied. Lastly, the protective layer 160 may be disposed on the top and the bottom. The protective layer 160 may consist of Poly(4-vinylpyridine-co-styrene) (PPS), but are not limited thereto.

Figure 3:
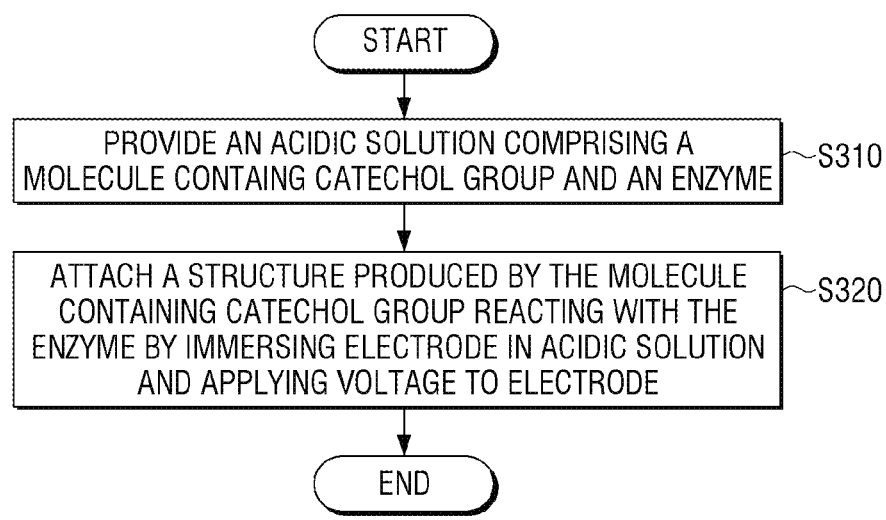
FIG. 3 is a flowchart provided to describe a manufacturing method of a bio-sensor according to an embodiment of the present disclosure.

FIG. 3 is a flowchart provided to describe a manufacturing method of a bio-sensor according to an embodiment of the present disclosure.

Referring to FIG. 3, an acidic solution including the molecule containing the catechol group and enzyme may be prepared S310. Then, a structure produced by reacting the molecule containing the catechol group with the enzyme by immersing the electrode in the acidic solution and applying a voltage to the electrode is attached to the electrode S320.

The catechol, not only performs a main role in strongly attaching to the electrode surface, but also may form a much stronger coating layer on the surface of the electrode crosslinked with each other by oxidization to quinine.

Specifically, voltage may be applied through Cyclic voltammetry to the electrode in step S320. In this case, a cycle may be repeated by a potential (for example, 250-400 mV) having a maximum oxidation efficiency. Further, applying a pulse type voltage or a predetermined constant voltage, that is, applying a constant voltage is also possible.

Figure 4:
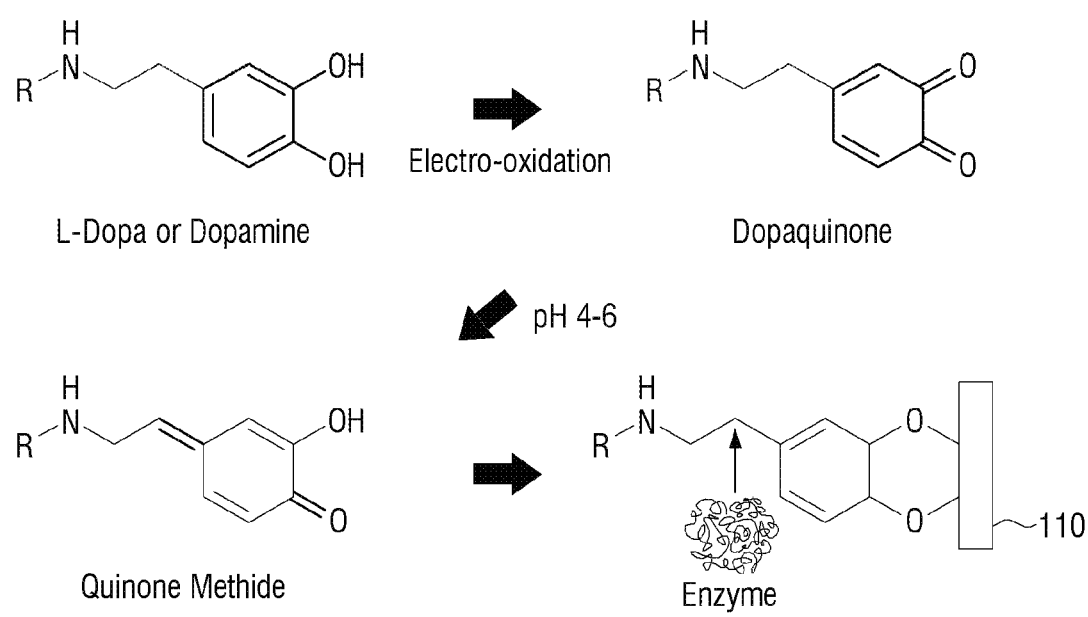
FIG. 4 is a diagram provided to show a covalent bonding of L-Dopa or electrochemical oxidization of Dopamine and enzyme.

Based on applying voltage to the electrode, the catechol group is electrochemically oxidized while at the same time covalently bonding to enzyme. An example of the reaction process is shown in FIG. 4 to more specifically describe the above. FIG. 4 is shows a molecule including L-Dopa residue or Dopamine residue as a molecule containing the catechol group.

Referring to FIG. 4, based on applying voltage to the electrode, the catechol group is electrically oxidized converting to Dopaquinine and Dopaquinine is converted to quinine methide in an acidic environment. The quinine methide is in a form that may be easily attacked by nucleophiles, and thus a composite may be obtained by covalent bonding to the enzyme by adding 1,4-Michael. The composite may bind to the electrode by hydrogen bonding, covalent bonding, or coordinate bonding according to a surface property of the electrode.

Based on using the electrochemical oxidization method such as the above, there may be more advantages rather than using a natural oxidation method. For example, if the catechol group is oxidized naturally, quinine and quinine methide, and other various derivatives may co-exist due to the slow rate of natural oxidation and an unwanted wide reaction of a dimer forming due to chemical bonding between derivatives may occur.

Whereas, in an electrochemical oxidization method, as it may take a mere few minutes in the entire electrochemical process, reaction time may be significantly reduced and the possibility of a side reaction occurring such as the above would be reduced.

In addition, based on oxidation occurring electrochemically in only areas selectively applied with potential, enzyme may be immobilized in only desired areas. Accordingly, based on the reference electrode not being influenced, short circuit may be prevented and there is the advantage of the process being simplified without undergoing multiple processes.

The present inventors have experimented the electrochemical oxidation under both an alkaline environment and an acidic environment, and have discovered that oxidation under an acidic environment results in the reduction of probability of the above-described undesired side reaction progressing. The inventors discovered that the pH of acidic solution provided in step S310 should preferably be adjusted to pH 4 to pH 6 to maximally prevent enzyme damage.

An enzyme layer may be formed on the surface of the electrode smoothly and uniformly within a short period of time under optimized reaction conditions such as the above. Accordingly, a high reaction efficiency may be obtained.

Figure 5:
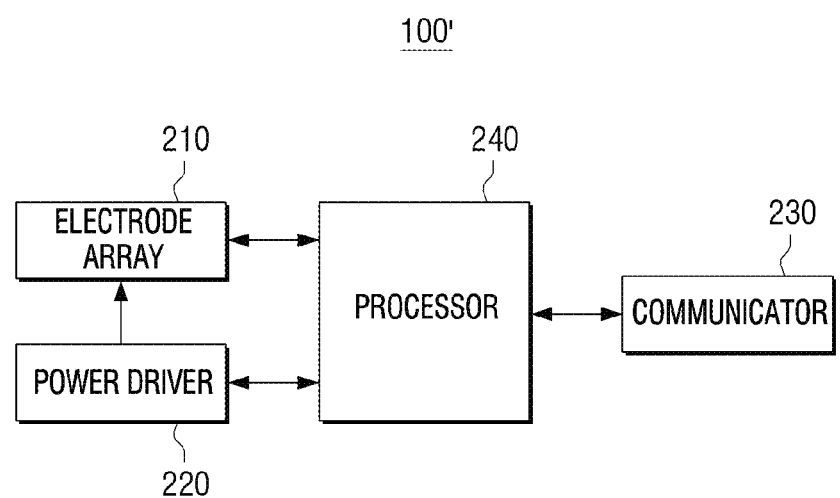
FIG. 5 is a diagram provided to describe a bio-senor having communication function with an external apparatus according to another embodiment of the present disclosure.

FIG. 5 is a diagram provided to describe a bio-senor having communication function with an external apparatus according to another embodiment of the present disclosure.

Referring to FIG. 5, the bio-sensor 100' includes an electrode array 210, a power driver 220, a communicator 230 and a processor 240.

An electrode array 210 includes a pair of electrodes, and by measuring the current flowing between the pair of electrodes, the target material may be quantified. Specifically, the electrode array 210 may include a working electrode and a reference electrode, and the working electrode is the immobilized enzyme electrode as described in FIGS. 1 to 4 above.

The power driver 220 is configured to provide voltage to the electrode array 210.

The power driver 220 may provide a voltage of any one form from a direct current (DC) voltage, alternating current (AC) voltage or a voltage superimposed with DC voltage and AC voltage to the electrode array 210.

The communicator 230 is a configuration for transmitting the measurement results of the bio-sensor 200 to an external apparatus. The communicator 230 is a configuration to perform communication with various external apparatuses, and may be connected not only in the form of connecting to an external apparatus through a Local Area Network (LAN) and an internet network, but also by a wireless communication (for example, wireless communication such as Z-wave, 4LoWPAN, RFID, LTE D2D, BLE, GPRS, Weightless, ZigBee, Edge Zigbee, ANT+, NFC, IrDA, DECT, WLAN, Bluetooth, WiFi, Wi-Fi Direct, GSM, UMTS, LTE, WiBRO, Cellular (3/4/5G), ultrasonic waves, etc.) method to an external device. The communicator may include various communication chips such as a WiFi chip, a Bluetooth chip, a wireless communication chip, or the like.

The processor 240 is configured to control the overall operation of the bio-sensor 100.

The processor 240 may control the power driver 220 to provide voltage to the electrode array 210. Specifically, the processor 240 may control the power driver 220 to provide a measured voltage for measuring the target material to the electrode array 210.

The measured voltage is a voltage value suitable for oxidizing only the target material, and may prevent other materials in the sample from oxidizing and adding to a current component. For example, based on the target material being glucose, the processor 240 may control the power driver 220 to provide a measured voltage of more than 0 to within 1 V.

The processor 240 detects the current flowing in the electrode array 210 as generated signal corresponding to the applied measured voltage, and performs a calculation using the same to calculate a concentration of target material. It is also possible to transmit the measured current vale to an external apparatus through the communicator 230 rather than directly calculating the concentration of the target material and having the concentration of the target material calculated in the external apparatus.

According to an embodiment, the processor 240 may include an analog digital converter (ADC), a calculator, and a memory. The current value may be input through the ADC, which may be converted to a digital value. The calculator may calculate the concentration value of the target material using the digital current value output from the ADC. Further, the calculated concentration value may be stored in the memory. The concentration value stored in the memory may be transmitted to an external apparatus through the communicator 230.

In this case, the external apparatus may be a device such as a smartphone. Accordingly, a user may confirm the measured blood glucose results through a smartphone of the like.

Hereinafter, the present disclosure will be described through the specific example and test examples. However, the example and test examples are merely illustrative to assist in the understanding of the present disclosure, and that the present disclosure is not limited by the example and test examples below.

EXAMPLE

Manufacturing a Blood Glucose Sensor

The manufacturing process will be described with reference to FIG. 2. A polyethylene terephthalate (PET) film is cut with a $CO_2$ laser to provide a main substrate 120 of a needle shape having a height and width of 1.5 mm and 700 μm, respectively, and a carbon as a working electrode is printed on the bottom and top surface of the main substrate 120 using a silk-screen print method. Further, an insulate layer 130 is disposed on the working electrode 110. Further, Ag/AgCl is used as a reference electrode 150.

In order to raise electron transfer efficiency from the enzyme to the electrode, Ferrocenecarboxylic acid as an electron-transfer mediator 111 is electrodeposited to the working electrode 110. Specifically, Ferrocenecarboxylic acid (10 mM) is dissolved in 100 mM TBAP in acetonitrile, the electrodes are then immersed in a solution and applied with a 25 time repeat cycle in a −0.2 V to 1.2 V voltage range (vs. Ag/AgCl) to perform electrodeposition, and washed in 100 mM phosphoric acid buffer solution (pH 7.4) by applying a potential of 0.1 V to 0.6 V (15 cycles). Next, the electron-transfer mediator 111 immerses the immobilized working electrode in distilled water for 10 minutes and dried at room temperature for 1 hour.

Figure 6:
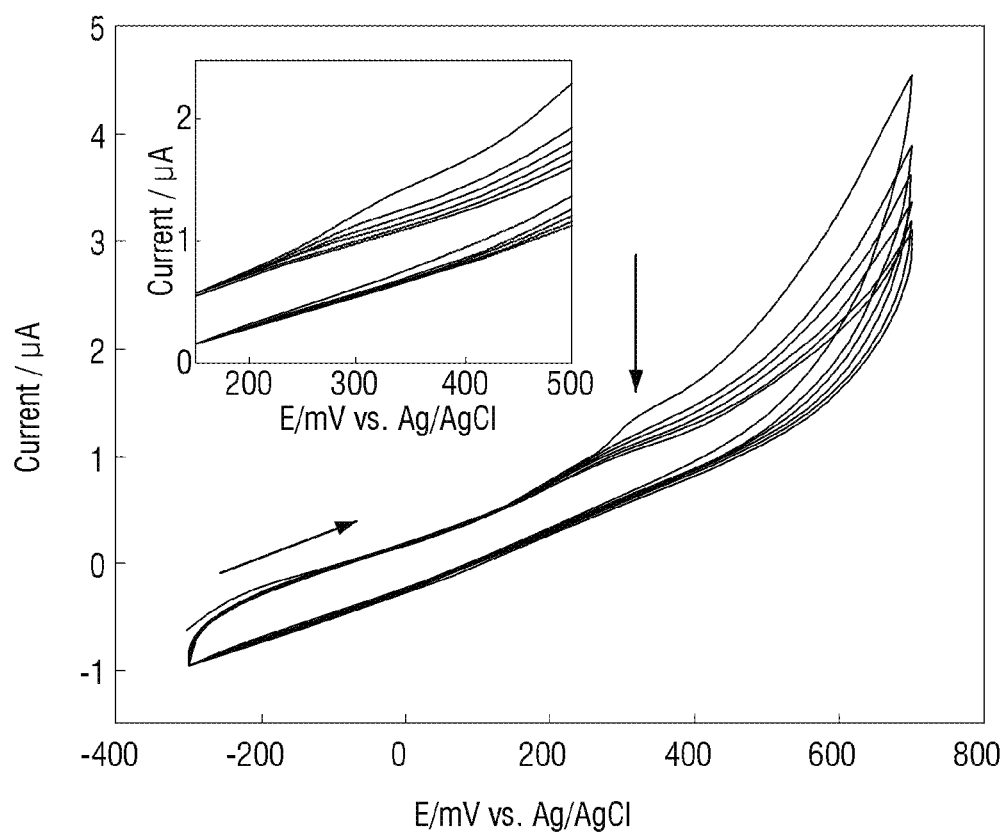
FIG. 6 is provided to show a measurement result according to Cyclic voltammetry on an electrochemical oxidization of a Mgfp-3 and glucose oxidase mixture.

In order to swiftly and selectively immobilize the enzyme, the Dopa residue of the mussel adhesive proteins is electrochemically oxidized in the present disclosure. A Mytilus galloprovincialis foot protein-3 (Mgfp-3; GenBank NO.: AAS00463), which is a type of mussel adhesive protein, is selected as a polymer matrix. Specifically, 2 mg/mL of Mgfp-3 and 200 mg/mL of GOx is dissolved in 10 mM of acetate buffer solution (pH 4). The Mgfp-3 and GOx mixture is electrolytically polymerized on the working electrode 110 through a potential cycle of −0.3 to 0.7 V (vs. Ag/AgCl) in a 100 mV/s scan rate (FIG. 6).

Figure 7:
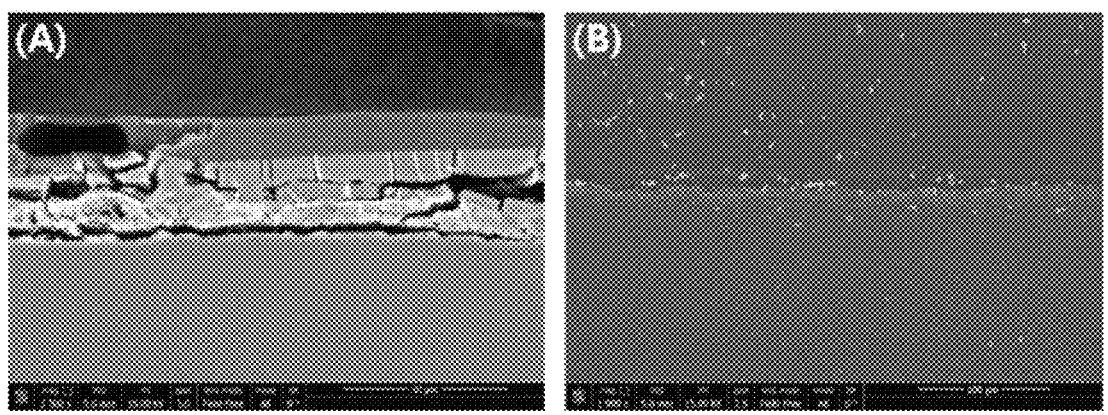
FIG. 7(*a*) is a scanning electron microscope (SEM) image provided to show a naturally oxidized Mgfp-3 and glucose oxidase reacting and forming a rough interface on the surface of an electrode under atmospheric condition.

The electrochemically oxidized Dopaquinine (Dopa-quinone) of Mgfp-3 is reacted with an amine or thiol of GOx to form a uniform enzyme layer (FIG. 7(9b)). In comparison, it can be confirmed that a voluntarily oxidized layer using the same mixture under ambient condition has a rough interface (FIG. 7(a)). A rough interface such as FIG. 7(a) reduces conductivity between the electrode and the enzyme and the sensitivity and reproducibility of a sensor is reduced. On the other hand, a uniform and smooth interface such as FIG. 7(b) contributes to a smooth electron flow between the electrode and the enzyme and improves sensitivity.

In a final step, the electrode immobilized with the electron-transfer mediator and GOx is immersed in 50% poly (4-vinylpyridine-co-styrene), then dried at room temperature for an hour, coated again in 30% poly(4-vinylpyridine-co-styrene), and dried at room temperature for 12 hours to form a protective layer 160.

Figure 8:
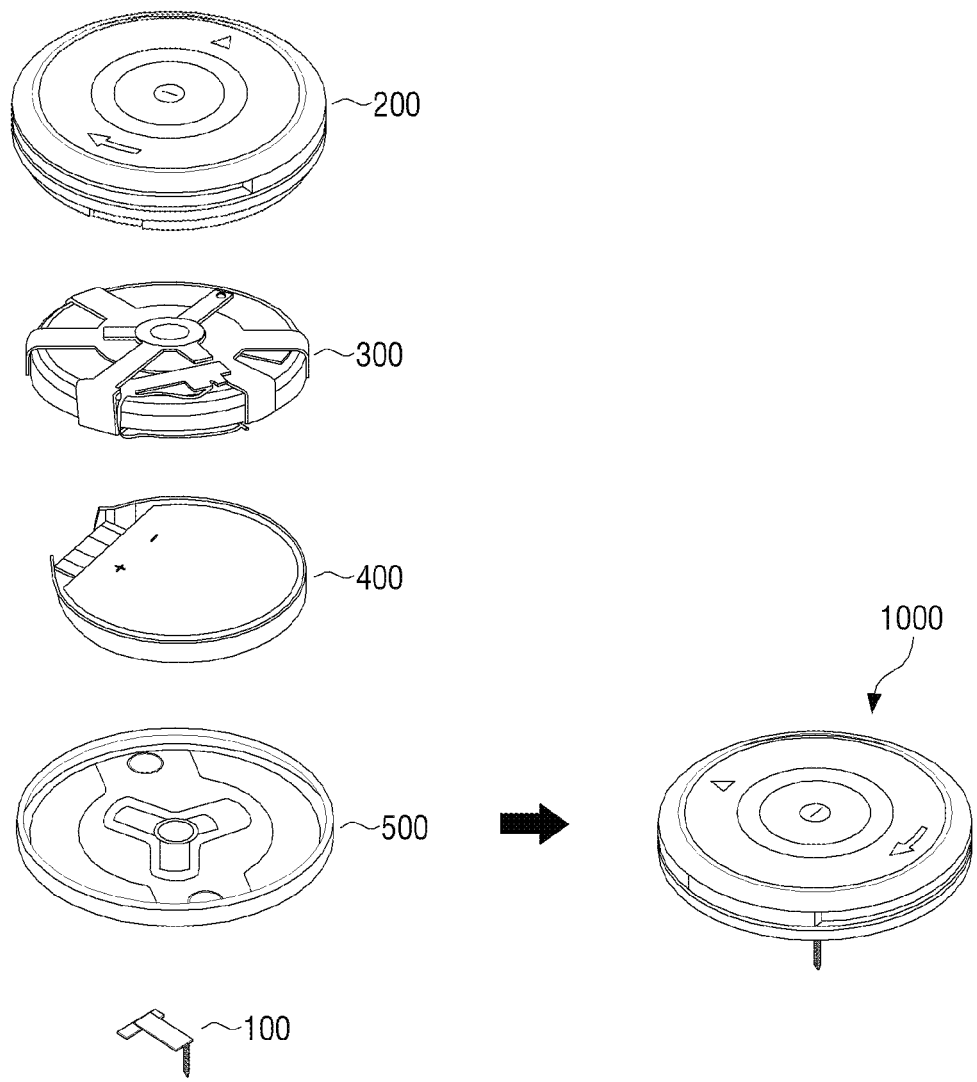
FIG. 8 is a diagram provided to describe a configuration of a sensor module according to an embodiment of the present disclosure.

A sensor module is manufactured using the bio-sensor 100 completed according to the above process. FIG. 8 shows a configuration of the sensor module.

Referring to FIG. 8, the sensor module 1000 includes a top surface cover 200 provided with an on/off switch, a communicator 300, a battery 400, a bottom surface cover 500, and a bio-sensor 100.

The communicator 300 includes a MCU (STM32F411, STMicro, CH), a small potentiostat, an analog-digital converter module (ADS1222, Texas Instruments, USA), a Bluetooth and a near field communication (NFC) module. The battery 400 uses a flexible lithium ion polymer battery (FLPB253030R, Routejade, KR).

The potentiostat applies a specifically operating potential to the sensor and measures the current generated by the oxidization glucose. The obtained analog data is amplified using the transimpedance amplifier (current-voltage converter) and is digitalized to a 24 bit analog-digital converter (ADC). Based on the transmitter continuously transmitting the current value of the sensor to a mobile phone equipped with a 2.4 GHz Bluetooth module (CSR1012, CSR, GB), the transmitter may provide a hypoglycemia warning to a diabetic patient. Using the transmitting NFC (M24LR64, STMicro, CH), the data stored in the transmitter memory may be transmitted to a mobile apparatus using 13.56 MHz of ISO15693.

Test Example 1

Detecting Glucose Using Chronoamperometry

Figure 9:
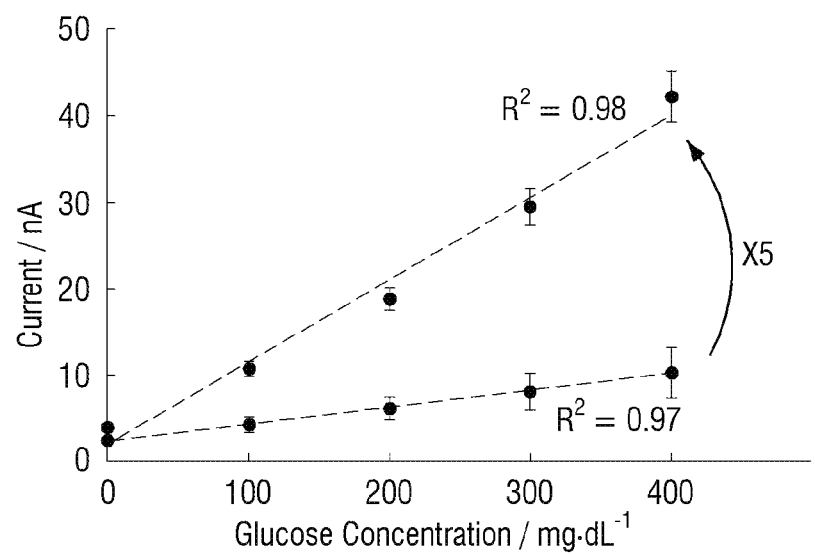
FIG. 9 is a Calibration plot provided to show a glucose concentration (from 0 to 400 mg·dL-1) of a conventional sensor and a sensor according to the present disclosure.

FIG. 9 is a calibration plot of current vs. glucose obtained by measuring response according to chronoamperometry by using a conventional sensor and the bio-sensor manufactured according to the above embodiment and applying an operational potential of 30 mV. FIG. 9 shows that the sensitivity of a glucose sensor according to the present disclosure is 9.57 nA/100 mg·dL-1 (R2=0.98), which is 5 times of that of a conventional glucose sensor that is 1.93 nA/100 mg·dL-1 (R2=0.97).

Figure 10:
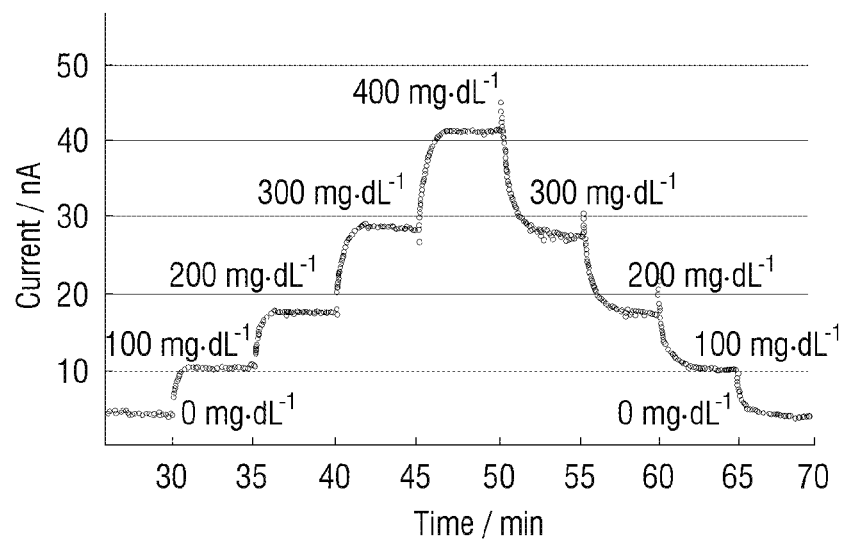
FIG. 10 is a graph provided to show an Amperometric current response of a sensor based on glucose increasing or decreasing sequentially.

The sensor response time is defined as a time spent on reaching 90% of a saturation amperometric response with respect to a particular glucose concentration. This parameter is related to a material transfer barrier added by the layer in the expansion of glucose and gluconic acid, which is an enzyme by-product, to achieve equilibrium with the change in glucose levels. FIG. 10 shows the sensor response based on the glucose sequentially increasing and decreasing. After each adding of the glucose, the sensor response time is approximately 60 seconds.

Test Example 2

Long-Term Stability Test

Figure 11:
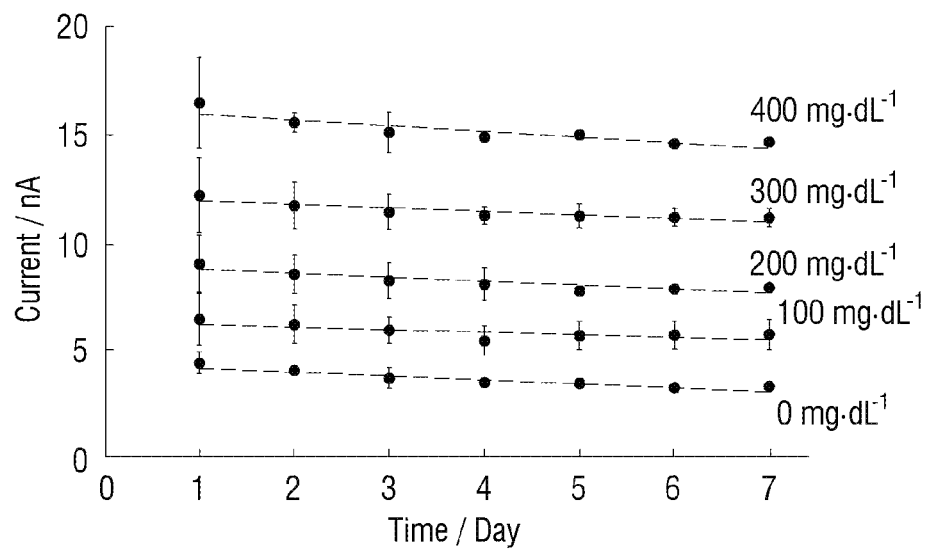
FIG. 11 is provided to show the result of testing the long-term stability of sensors for 7 days.

The long-term stability of the bio-sensor manufactured according to the above embodiment uses five different glucose concentrations (0-400 mg·dL-1) and has assessed for a period of 7 days. The operating potential is reduced from 30 mV to 10 mV to extend stability (FIG. 11). During testing, the sensor is exposed to all glucose concentrations and tested 10 times, and when not in testing, potential is applied and the sensor is immersed in 100 mg/dL-1 glucose standard solution. As shown in FIG. 11, the error on day 1 is shown as greater than any other days, but current response is stabilized after 30 minutes and the CV value is within 4.82%, nearly similar to the initial value.

Test Example 3

Analysis on Influence by Interfering Materials Based on Measurement of Glucose

Figure 12:
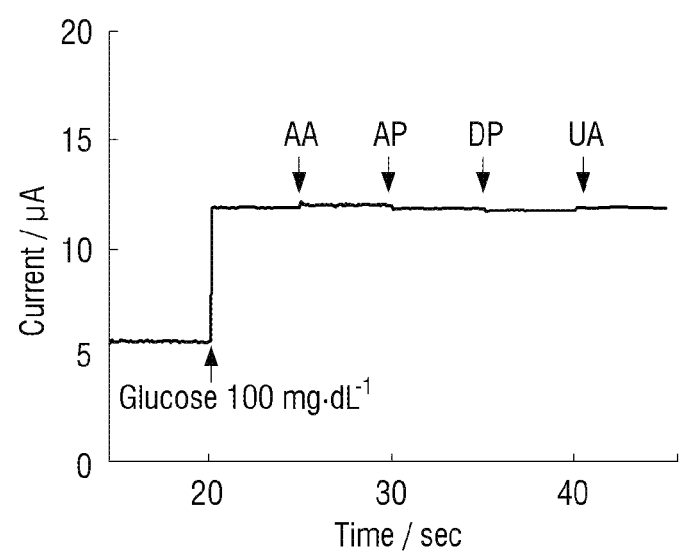
FIG. 12 is a diagram provided to describe the obstruction effect concerning Ascorbic acid (AA), Acetaminophen (AP), Dopamine (DA), and Uric acid (UA) based on measuring glucose with a sensor of the present disclosure.

FIG. 12 measures the glucose oxidation current of the bio-sensor manufactured according to an above embodiment based on the presence of interfering materials such as an ascorbic acid (AA), an acetaminophen (AP), a Dopamine (DP) and an uric acid (UA).

The interfering materials have an oxidation potential similar to glucose, and may influence the glucose response signal. All interfering materials are dissolved in PBS (pH 7.4) at 100 μM, and based on the existence of the interfering materials through chronoamperometry, signal changes of glucose have been observed. FIG. 12 shows a change in measured current response for a control and a test samples applied with a potential of 30 mV. As a result, a marginal error of approximately 3% or less is observed.

While the disclosure has been shown and described with reference to the exemplary embodiment thereof, the present disclosure is not limited to the specific embodiments described above. It will be understood by those of ordinary skill in the art that various changes in form and details may be made therein without departing from the spirit and scope of the disclosure, and these various changes in form and details should not be understood as individual from the technical idea or scope of the present disclosure.

What is claimed is:

1. A manufacturing method of a bio-sensor, the method comprising:
    preparing an acidic solution comprising a molecule containing a catechol group and an enzyme; and
    attaching a structure produced by the molecule containing the catechol group reacting with the enzyme by immersing an electrode in the acidic solution and applying a voltage to the electrode.

2. The manufacturing method of a bio-sensor according to claim 1, wherein a pH of the acidic solution is pH 4 to pH 6.

3. The manufacturing method of a bio-sensor according to claim 1, wherein the structure is produced by binding the molecule comprising a quinone methide group derived by electrochemically oxidizing the molecule containing the catechol group in an acidic environment with the enzyme.

4. The manufacturing method of a bio-sensor according to claim 1, wherein the attaching comprises applying a voltage to the electrode by cyclic voltammetry.

5. The manufacturing method of a bio-sensor according to claim 1, wherein the attaching comprises applying a voltage of a pulse type voltage to the electrode.

6. The manufacturing method of a bio-sensor according to claim 1, wherein the attaching comprises applying a predetermined constant voltage to the electrode.

7. The manufacturing method of a bio-sensor according to claim 1, wherein the molecule containing the catechol group is derived from a mussel adhesive protein.

8. The manufacturing method of a bio-sensor according to claim 1, wherein the electrode is needle shaped to be invasive to skin.

9. The manufacturing method of a bio-sensor according to claim 1, wherein the enzyme is selected from a group consisting of glucose oxidase, glucose dehydrogenase, hexokinase, glutamic-oxaloacetic transaminase and glutamic-pyruvic transaminase.

10. A bio-sensor, comprising: an electrode; and a structure attaching to a surface of the electrode and formed by binding a molecule comprising quinone methide group with an enzyme.

11. The bio-sensor according to claim 10, wherein the molecule comprising the quinone methide group is derived by electrochemically oxidizing the molecule containing the catechol group in an acidic environment.

12. The bio-sensor according to claim 10, wherein the electrode is needle shaped to be invasive to skin.

13. The bio-sensor according to claim 10, wherein the enzyme is selected from a group consisting of glucose oxidase, glucose dehydrogenase, hexokinase, glutamicoxaloacetic transaminase and glutamic-pyruvic transaminase.

* * * * *